(12) United States Patent
Slater

(10) Patent No.: US 10,983,366 B2
(45) Date of Patent: *Apr. 20, 2021

(54) EYEWEAR FOR TREATMENT OF VESTIBULAR MALADIES

(71) Applicant: Patrick Slater, Austin, TX (US)

(72) Inventor: Patrick Slater, Austin, TX (US)

(*) Notice: Subject to any disclaimer, the term of this patent is extended or adjusted under 35 U.S.C. 154(b) by 50 days.

This patent is subject to a terminal disclaimer.

(21) Appl. No.: 15/181,705

(22) Filed: Jun. 14, 2016

(65) Prior Publication Data
US 2017/0357109 A1    Dec. 14, 2017
US 2020/0124876 A9    Apr. 23, 2020

Related U.S. Application Data

(63) Continuation of application No. 13/665,862, filed on Oct. 31, 2012, now Pat. No. 9,395,556.

(60) Provisional application No. 61/553,827, filed on Oct. 31, 2011.

(51) Int. Cl.
| | | |
|---|---|---|
| *G02C 7/10* | (2006.01) | |
| *G02C 7/06* | (2006.01) | |
| *G02C 7/12* | (2006.01) | |
| *A61B 5/00* | (2006.01) | |

(52) U.S. Cl.
CPC .......... *G02C 7/105* (2013.01); *A61B 5/4023* (2013.01); *G02C 7/06* (2013.01); *G02C 7/104* (2013.01); *G02C 7/12* (2013.01); *G02C 2202/10* (2013.01)

(58) Field of Classification Search
CPC ... A61B 5/4023; A61B 5/4076; A61B 5/4005; A61B 5/40; A61F 2/16; A61F 2/1613; A61F 2/1602; A61F 2/1618; A61F 9/00; A61H 5/00; A61H 5/005; G02B 5/223; G02B 27/0025; G02C 5/001; G02C 7/02; G02C 7/021; G02C 7/04; G02C 7/042; G02C 7/044; G02C 7/06; G02C 7/061; G02C 7/066; G02C 7/08; G02C 7/086; G02C 7/10; G02C 7/104; G02C 7/105; G02C 7/12; G02C 2202/10
USPC ....... 351/41, 44, 49, 54, 57, 159.01, 159.24, 351/159.31, 159.41, 159.42, 159.43, 351/159.49, 159.59, 159.63, 159.64, 351/159.65, 159.73, 159.75, 159.78, 351/159.79, 159.81, 203, 246; 434/184;
(Continued)

(56) References Cited

U.S. PATENT DOCUMENTS

| | | | | |
|---|---|---|---|---|
| 4,979,902 A | * | 12/1990 | Morelle | .......... A61H 5/00 351/246 |
| 5,440,359 A | * | 8/1995 | Bloch-Malem | ........ G02C 7/104 351/159.24 |
| 10,241,350 B1 | * | 3/2019 | Poulsen | .......... G02C 7/14 |

(Continued)

*Primary Examiner* — William R Alexander
(74) *Attorney, Agent, or Firm* — John A. Fortkort; Fortkort & Houston PC

(57) ABSTRACT

A method for treating a patient having a vestibular malady is provided. The method comprises (a) diagnosing the patient as having a vestibular malady; and (b) prescribing eyewear to the patient as a treatment of the vestibular malady, either alone or in conjunction with undertaking vestibular rehabilitation while wearing the eyewear. The eyewear (201) has a first lens (205) which extends over the field of vision of a first eye, wherein the first lens has first (207) and second (209) distinct optical regions. The eyewear imparts vision to the first eye which is characterized by a central vision having a first optical quality and a peripheral vision having a second optical quality.

30 Claims, 3 Drawing Sheets

(58) Field of Classification Search
USPC .............. 600/300, 558, 559; 604/289, 294; 607/137; 623/6.11, 6.27, 6.3
See application file for complete search history.

(56) References Cited

U.S. PATENT DOCUMENTS

| | | | | |
|---|---|---|---|---|
| 2002/0099257 A1* | 7/2002 | Parker | ................ | G02B 27/0093 600/27 |
| 2009/0312817 A1* | 12/2009 | Hogle | .................... | G06F 3/012 607/54 |
| 2011/0066067 A1* | 3/2011 | Zelinsky | ................ | A61B 5/411 600/558 |
| 2013/0107206 A1* | 5/2013 | Slater | .................... | G02C 7/021 351/159.78 |

* cited by examiner

EYEWEAR FOR TREATMENT OF VESTIBULAR MALADIES

CROSS REFERENCE TO RELATED APPLICATION

This application is a continuation application which claims the benefit of priority from U.S. application Ser. No. 13/665,862, filed Oct. 31, 2012, having the same title, and having the same inventor, and which is incorporated herein by reference in its entirety. This application also claims the benefit of priority from U.S. Provisional Application No. 61/553,827, filed Oct. 31, 2011, having the same title, and having the same inventor, and which is incorporated herein by reference in its entirety.

TECHNICAL FIELD OF THE INVENTION

The present disclosure pertains generally to the treatment of vestibular maladies, and more particularly to the use in such treatment of eyewear which imparts tunnel vision to the user, thus causing subtle inner ear reflexes to improve activity.

BACKGROUND OF THE INVENTION

Vestibular rehabilitation therapy (VRT) is currently utilized in the medical arts to treat a variety of vestibular maladies, such as benign paroxysmal positional vertigo (BPPV), labyrinthitis, vestibular neuritis, and the unilateral or bilateral vestibular hypofunction (reduced inner ear function on one or both sides) that is commonly associated with Ménière's disease. However, VRT is believed to work best in the treatment of stable vestibular maladies. VRT is also useful in treating patients with an acute or abrupt loss of vestibular function subsequent to surgery for vestibular problems. In some cases, it is found that patients with long-term, unresolved inner ear disorders, who have undergone a period of medical management with little or no success, may also benefit from VRT.

Vestibular problems affect the vestibulo-ocular reflex (VOR), which controls eye movement and gaze stabilization during head movement, and may also affect the vestibulospinal reflex (VSR), which influences postural stability. Consequently, one of the goals of VRT is to improve these reflexes. VRT does not repair the damaged inner ear, but focuses instead on helping the central nervous system to adapt to the asymmetrical input from the VOR and VSR. Without wishing to be bound by theory, such adaptation may occur through the spontaneous rebalancing of tonic activity in the vestibular nuclei, or by the recovery of the VOR through adaption or by way of the abituation effect (which lessens the response to the same stimuli over time).

VRT typically includes three main approaches: canalith repositioning, substitution and adaption. Canalith repositioning is an option for patients having BPPV in conjunction with labyrinthitis, and involves repositioning calcium crystals into the correct inner ear canal.

Substitution involves strengthening the vestibular system by reducing other inputs such as, for example, vision. In this approach, an exercised regime may be prescribed, but may be performed, for example, with the eyes closed.

Adaption is designed to reset the VOR. Typically, this is accomplished through an exercise regime which features head positions and movements the patient has been avoiding. Many of the exercises feature head movement with eye movement, and often utilize different surfaces. For example, the patient may start an exercise session standing on carpet, and then progress to foam during the exercise. Adaption aids rehabilitation by causing the vestibular system to work harder.

It will be appreciated from the foregoing that, in substitution and adaption approaches, VRT is frequently implemented as an exercise-based program designed to promote central nervous system compensation for inner ear deficits. In a typical VRT regimen of this type, a qualified physical therapist or occupational therapist performs a thorough evaluation that includes an examination of the patient's medical history and an assessment of the patient's VSR. This assessment includes observing and measuring posture, balance and gait, and compensatory strategies. The assessment may also include eye-head coordination tests that measure how well a person's eyes track a moving object (with or without head movement). The therapist may also administer a suitable questionnaire designed to measure the frequency and severity of symptoms and associated lifestyle changes.

Using the evaluation results, the therapist will develop an individualized treatment plan that includes specific head, body, and eye exercises to be performed both in the therapy setting and at home. These exercises are designed to retrain the brain to recognize and process signals from the vestibular system and to coordinate them with visual information and proprioception. This often involves desensitizing the balance system to movements that provoke symptoms, and increasing home-based activities and exercise in order to strengthen muscles. Home exercises are often a vital part of treatment, and the therapist will frequently design an individualized treatment plan with appropriate exercises to be performed by the patient at home at a prescribed pace.

SUMMARY OF THE INVENTION

In one aspect, a method for treating a patient having a vestibular malady is provided. The method comprises (a) diagnosing the patient as having a vestibular malady; and (b) prescribing eyewear to the patient having a first lens which extends over the field of vision of a first eye, wherein the first lens has first and second distinct optical regions which impart vision to the first eye, and wherein the imparted vision is characterized by a central vision having a first optical quality and a peripheral vision having a second optical quality which is distinct from the first optical quality. The eyewear may be used either as a stand-alone treatment of the vestibular malady, or may be used in conjunction with vestibular rehabilitation (for example, the patient may undertake vestibular rehabilitation, such as a vestibular rehabilitation therapy session, while wearing the eyewear).

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

While conventional vestibular rehabilitation therapy (VRT) is effective in treating some patients who suffer from vestibular maladies, further improvements in the treatment of vestibular maladies, and in the efficacy of VRT, is desired.

It has now been found that this objective may be attained by utilizing the eyewear described herein, either as a stand-alone treatment for treating vestibular maladies, or as a tool to be used in conjunction with VRT. When used in conjunction with VRT, the effectiveness of VRT may be enhanced by having the patient wear the eyewear described herein during the VRT therapy sessions. This eyewear is equipped with a first lens which extends over the field of vision of a first eye, wherein the first lens has first and second distinct optical regions which impart vision to the first eye which is characterized by first and second optical characteristics, respectively.

Preferably, the eyewear is further equipped with a second lens which has similar optical properties to the first lens. In particular, the second lens preferably extends over the field of vision of a second eye, and has third and fourth distinct optical regions which impart vision to the second eye which is characterized by third and fourth optical characteristics, respectively. Preferably, the first and third optical regions have the same optical characteristics, and the second and fourth optical regions have the same optical characteristics. Even more preferably, the first and third optical regions impart an undistorted central vision to the eyes of a person wearing the eyewear, and the second and fourth optical regions impart a distorted peripheral vision to the eyes of a person wearing the eyewear.

Figure 1:
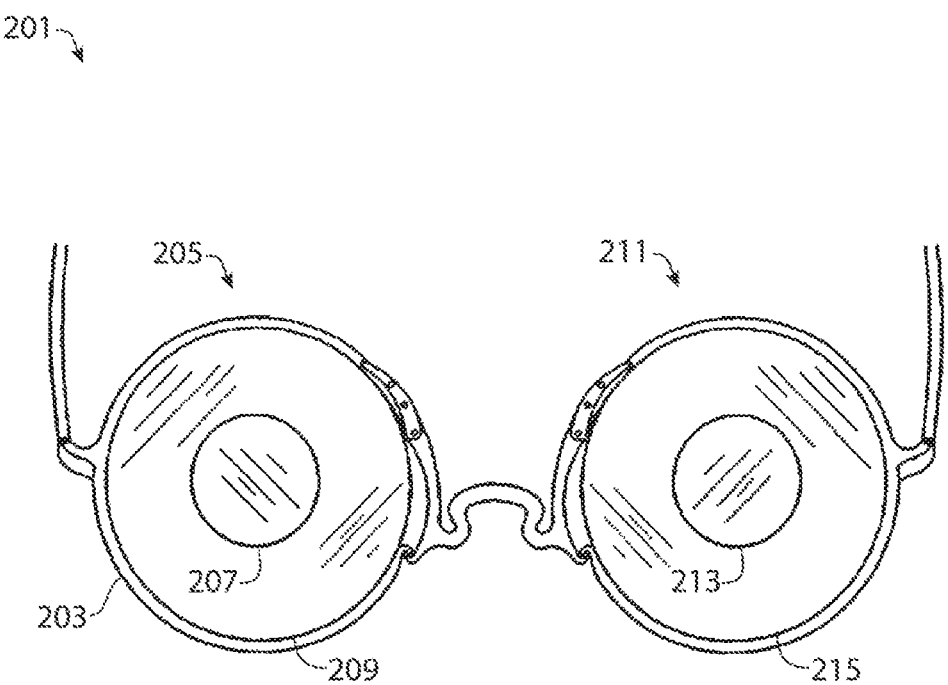
FIG. 1 is an illustration of a first particular, non-limiting embodiment of a set of eyeglasses made in accordance with the teachings herein.

FIG. 1 discloses a first particular, non-limiting embodiment of eyewear which may be utilized in the practice of the methodologies disclosed herein. The eyewear 201 disclosed therein is a set of eyeglasses having first 205 and second 211 lenses. As used herein, the term "lens" refers merely to a portion of the eyeglasses that covers a portion of the user's field of vision, and does not by itself imply any particular optical characteristic or effect. The first lens 205 has first 207 and second 209 regions defined therein, and the second lens 211 has third 213 and fourth 215 regions defined therein. Any of the first 207, second 209, third 213 and fourth 215 regions may be optical regions (that is, may impart an optical effect to the user's vision). These regions may be placed in various locations in the lenses, but preferably, the first 207 and third 213 regions are situated within the lens so that they are disposed over all or a portion of the central portion of the user's vision, and the second 209 and fourth 215 regions are situated within the lens so that they are disposed over all or a portion of the peripheral portion of the user's vision.

In one preferred embodiment, the optical characteristics of the first 207 and third 213 regions are the same, and the optical characteristics of the second 209 and fourth 215 regions are the same, although embodiments are also possible in which the optical characteristics of any of the first 207, second 209, third 213 and fourth 215 optical regions may independently be the same or different. For example, in one preferred embodiment, the color and/or tinting of the first 207 and third 213 regions is the same, the color and/or tinting of the second 209 and fourth 215 regions is the same, and the color and/or tinting of the first 207 and second 209 regions is different.

Even more preferably, the first 207 and third 213 regions may have a lesser degree of color and/or tinting (and preferably, no color or tinting) (as measured, for example, by darkness, saturation or hue), and the second 209 and fourth 215 regions may have a greater degree of color and/or tinting (and preferably, a pronounced degree of color and/or tinting). This has the effect of dimming the peripheral portion of the user's vision, thus creating a tunnel vision effect of the type referred to above which is characterized by clear and bright central vision and a darkened peripheral vision.

In another preferred embodiment, the optical power of the first 207 and third 213 regions is the same, and the optical power of the second 209 and fourth 215 regions is the same. Preferably, the first 207 and third 213 regions impart normal (e.g., 20/20) vision to the user in the field of vision they cover, and hence, the optical characteristics of this region may be selected in light of the user's vision. By contrast, the optical characteristics of the second 209 and fourth 215 regions are preferably selected to impart other than 20/20 vision to the user, and more preferably are selected to impart distorted, blurred, or occluded vision to the user in the field of vision they cover. Most preferably, the optical characteristics of the second 209 and fourth 215 regions are selected so that, taken in conjunction with the first 207 and third 213 regions, the eyewear imparts a condition of tunnel vision or near-sightedness to the user which is characterized by clear central vision and a peripheral vision that is distorted or "out-of-focus".

Various means may be utilized to create regions with different optical characteristics for the purposes of the teachings herein. The optical characteristics may be, for example, color, tint, optical power, polarization, specularity, diffusiveness, degree of clarity, degree of obfuscation, optical reflectivity (over one or more wavelengths), optical transmission (over one or more wavelengths), the presence or absence of visual artifacts, degree of vision correction, or various combinations or subcombinations of the foregoing.

Figure 2:
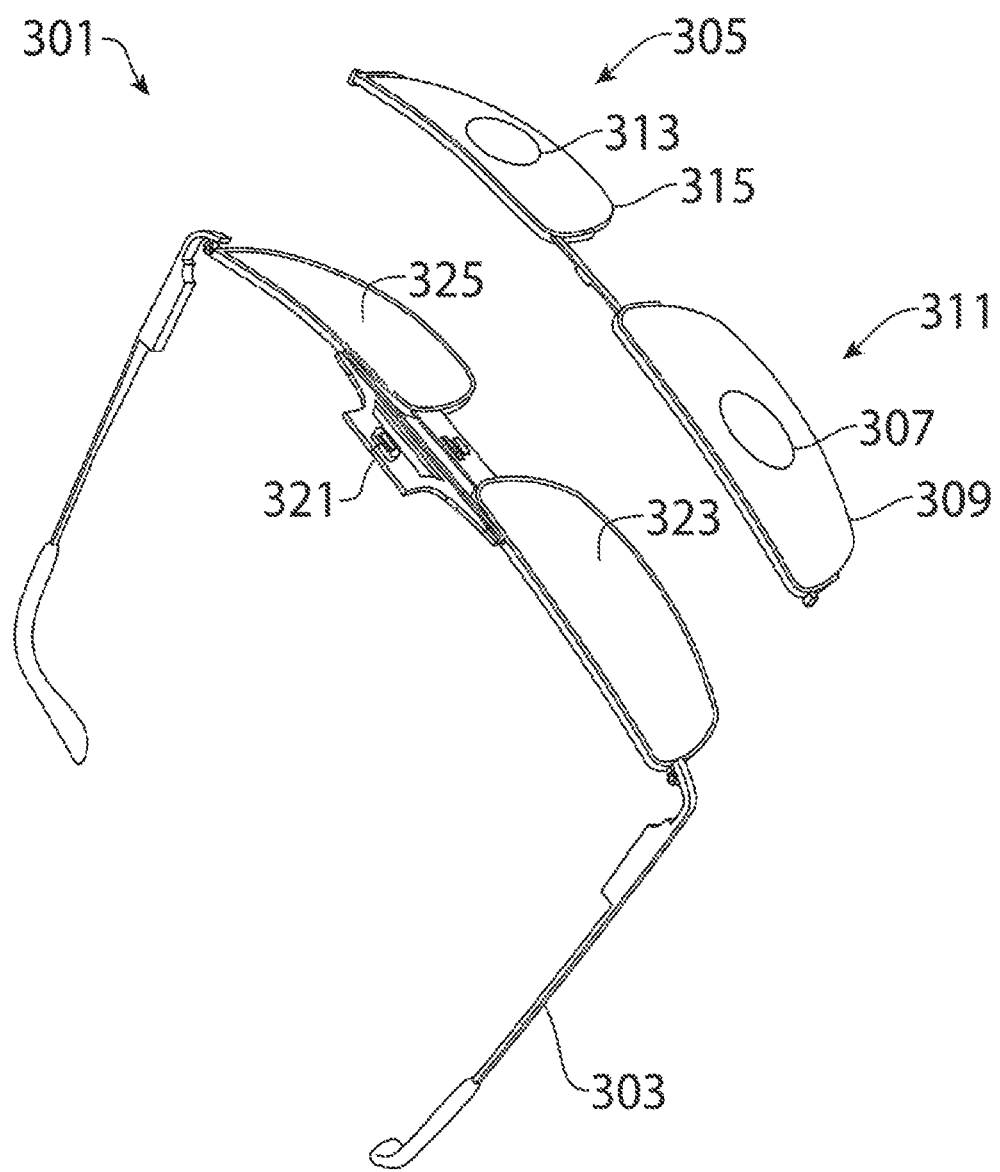
FIG. 2 is an illustration of a second particular, non-limiting embodiment of a set of eyeglasses made in accordance with the teachings herein.

FIG. 2 illustrates a second particular, non-limiting embodiment of eyewear which may be utilized in the methodologies described herein. The eyewear 301 in this embodiment comprises a set of glasses 302 equipped with a clip 321 that releasably engages a flip frame 319. The glasses 302 are otherwise conventional and comprise a first frame 303 within which is set first 323 and second 325 lenses. In some implementations of this embodiment, the glasses 302 may be prescription glasses to impart corrected (and hence normal) vision to users with vision problems. In other implementations, the glasses may simply comprise clear glass or plastic that does not provide any vision correction.

The flip frame 319 comprises a second frame 333 within which is set a first 305 lens comprising first 307 and second 309 regions, and a second 311 lens comprising third 313 and fourth 315 regions. The first 305 and second 311 lens, and the first 307, second 309, third 313 and fourth 315 regions may be of the type described with respect to their analogous components in the embodiment depicted in FIG. 1.

In use, when it is desired to impart tunnel vision, near-sightedness, or to otherwise modify the user's vision for the purposes described herein, the user simply flips the flip frame 319 into place over the first 323 and second 325 lenses, whereupon the eyewear 301 functions in a manner similar to the eyewear of FIG. 1. Hence, this embodiment provides the user with ready access to the advantages of the eyewear described herein, while also providing the user with the protection or use of conventional eyewear when such advantages are not needed.

Figure 3:
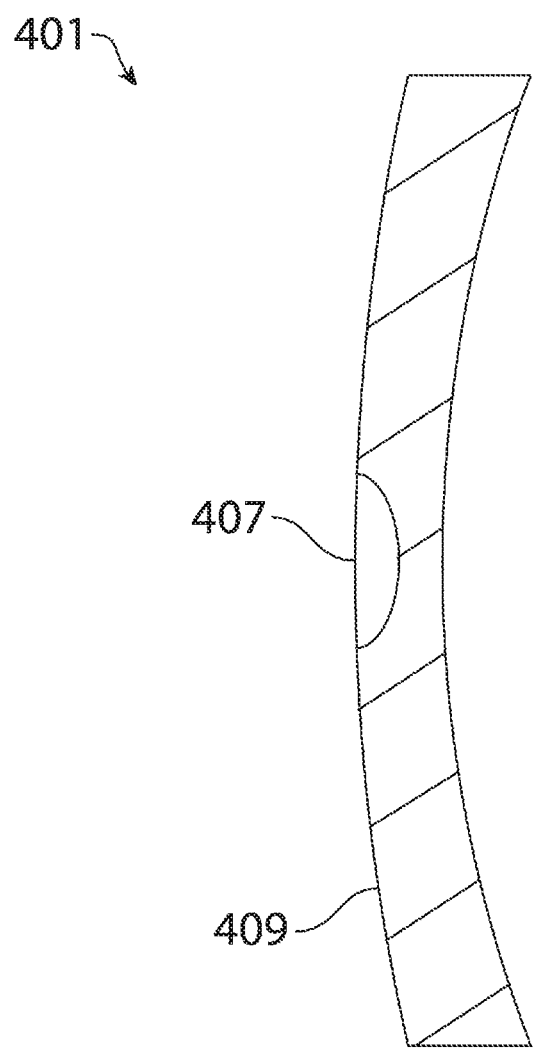
FIG. 3 is an illustration of a particular, non-limiting embodiment of an ophthalmic lens made in accordance with the teachings herein.

FIG. 3 illustrates a second particular, non-limiting embodiment of eyewear which may be utilized in the methodologies described herein. The eyewear 401 in this embodiment comprises an ophthalmic lens 401 having first 407 and second 409 optical regions defined therein. As in the embodiments described above, the first 407 and second 409 optical regions preferably cooperate to induce tunnel vision or short-sightedness in the user. Methods which may be used to make an ophthalmic lens of this type are described in U.S. Pat. No. 7,472,993 (Matsui), which is incorporated herein by reference.

In some of the embodiments described herein, it may be desirable to construct lenses having a first region characterized by a first degree of optical distortion $d_1$ and a second region characterized by a second degree of optical distortion $d_2$, wherein $d_1 < d_2$. In such embodiments, $d_1$ may be very small or may be essentially 0, and $d_2$ may be in the range, for example, of greater than 2%, greater than 5%, greater than 10%, or greater than 20%.

Various methodologies for measuring the degree of optical distortion may be utilized in fabricating such embodiments. One such methodology is described, for example, in the ASTM F2156-11 standard entitled "Standard Test Method for Measuring Optical Distortion in Transparent Parts Using Grid Line Slope". In some implementations of this type of embodiment, the optical distortion may maintain or expand the image in the center of the field of view and compress the image in the periphery of the field of view. Examples of lenses capable of performing such a functionality may be found, for example, in U.S. 2012/0206627 (Reshidko et al.), which is incorporated herein by reference in its entirety.

In some of the embodiments described herein, it may be desirable to construct lenses having a first region characterized by a first % transmission $T_1$ to visible light and a second region characterized by a second % transmission $T_2$ to visible light. In such embodiments, the difference in % transmission $(T_1-T_2)$ is preferably at least 10%, more preferably at least 20%, even more preferably at least 30%, and most preferably in the range of about 25% to about 50%. The % transmission may be expressed in various ways including, for example, the average transmission over the visible region of the spectrum, or the minimum or maximum transmission over the visible region of the spectrum.

In some of the embodiments described herein, it may be desirable to construct lenses having a first region characterized as being relatively free of optical occlusions, and a second region which contains optical occlusions. The occlusions may be, for example, particles or features which specularly or diffusely scatter, reflect light or absorb light over the visible region of the spectrum. Preferably, the first region is essentially devoid of such optical occlusions so that it provides little or no scattering, reflection or absorption of visible light, while the second region provides at least some scattering, reflection or absorption of visible light. The amount of scattering, reflection or absorption of visible light in the second region may be, for example, at least 10%, at least 20%, at least 30%, or at least 50%, but is preferably within the range of about 25% to about 50%, while the amount of scattering, reflection or absorption of visible light in the first region is preferably less than 10%, more preferably less than about 5%, and even more preferably less than about 2%. The % of scattering, reflection or absorption may be expressed in various ways including, for example, the average scattering, reflection or absorption over the visible region of the spectrum, or the minimum or maximum scattering, reflection or absorption over the visible region of the spectrum.

In some embodiments, the second region may have visible features (such as, for example, printed features) disposed thereon or therein, and the first region may be free of such features or contain a lower incidence of them. The features may include, for example, dots, lines, curves, geometrical figures or patterns, or the like. In other embodiments, perforations in the lenses may be used in place of, or in addition to, such features.

In some of the embodiments described herein, it may be desirable to construct lenses having a first region characterized as having a higher transmission or a lower reflectivity or absorption, and a second region characterized as having a lower transmission or a higher reflectivity or absorption. This may be accomplished, for example, by providing or applying an optically reflective or absorbing film to (or over) the second region but not to (or over) the first region, or by providing an optically reflective or absorbing film to (or over) both regions and selectively removing it from the first region. A similar effect may be provided by applying an optically reflective or absorbing pigment to (or over) the second region but not to (or over) the first region, by providing a higher density of the reflective or absorbing pigment or film to (or over) the second region than the first region, or by applying first and second reflective or absorbing films to the first and second regions, wherein the second reflective film has a higher reflectivity than the first reflective film.

In any of the foregoing embodiments, the reflective films or pigments may also be polarizing films or pigments. Moreover, the optical reflectivity or absorption of the second region to visible light may be, for example, at least 10%, at least 20%, at least 30%, or at least 50%, but is preferably within the range of about 25% to about 50%, while the optical reflectivity or absorption of the first region to visible light is preferably less than 10%, more preferably less than about 5%, and even more preferably less than about 2%.

In some of the embodiments described herein, it may be desirable to construct lenses in which the first region is characterized as having a first color or hue (or being colorless), and in which the second region is characterized as having a second color or hue. The first and second colors or hues are preferably distinct, but may also (or instead) differ in value or saturation. Preferably, the second color is darker or cooler (e.g., more towards the blue end of the spectrum) than the first color. Most preferably, the first region is colorless, and the second region is selected from the group consisting of green, blue or violet.

The first, second, third and fourth regions may have various shapes and may independently be, for example, elliptical, circular, polygonal (including, for example, square, rectangular, pentagonal, hexagonal and octagonal), or irregular in shape.

The dimensions of the first, second, third and fourth regions may vary from one implementation to another. Typically, the first and third regions have a major dimension within the range of about 4 mm to about 75 mm, preferably within the range of about 8 mm to about 50 mm, more preferably within the range of about 15 mm to about 35 mm, and most preferably within the range of about 20 mm to about 30 mm. The dimensions of the second and fourth regions may also vary, and will typically be dictated by such considerations as style, gender of the user, the dimensions of popular or available frames, and the like.

In some embodiments, the boundaries between the first and second regions and the third and fourth regions may be sharply defined. In other embodiments, these regions may be blurred, may transition gradually into each other, or may be separated from each other by an intervening region which may be optically distinct from the first and second regions.

While the eyewear disclosed herein has frequently been described as lenses having two distinct optical regions thereon, one skilled in the art will appreciate that, in some embodiments, a larger number of optical regions may be utilized to a similar effect.

All references, including publications, patent applications, and patents, cited herein are hereby incorporated by reference to the same extent as if each reference were individually and specifically indicated to be incorporated by reference and were set forth in its entirety herein.

As used herein, the term "essentially", as used in reference to a geometric shape or figure (e.g., "essentially elliptical"), means that one skilled in the art would describe the item in question as having the designated shape or figure, notwithstanding slight deviations or imperfections in the item that might prevent it from meeting the strict mathematical definition of such a shape or figure. When used in reference to a number k, "essentially" k shall mean k±0.05k. Moreover, the disclosure of "essentially" k shall be taken to be a disclosure of both "essentially" k and k as possible values for the parameter in question.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating a patient having a vestibular malady, comprising:

diagnosing the patient as having a vestibular malady; and
treating the vestibular malady by causing the patient to undertake vestibular rehabilitation while wearing eyewear, wherein the vestibular rehabilitation includes a series of physical exercises, wherein the eyewear has a first lens which extends over the field of vision of a first eye, wherein the first lens has first and second distinct optical regions which impart vision to the first eye which is characterized by a central vision having a first optical quality and a peripheral vision having a second optical quality, wherein the first central vision has a first optical quality that is not shared by the first peripheral vision, wherein the second optical region distorts the peripheral vision of the first eye, and wherein the first optical region does not distort the vision of the first eye along the line of sight.

2. The method of claim 1, wherein the vestibular rehabilitation includes a series of physical exercises to strengthen the vestibulo-ocular reflex (VOR).

3. The method of claim 1, wherein the vestibular rehabilitation includes a series of physical exercises designed to strengthen the vestibulospinal reflex (VSR).

4. The method of claim 1, wherein the vestibular rehabilitation implements an adaption approach.

5. The method of claim 1, wherein the vestibular rehabilitation implements a substitution approach.

6. The method of claim 1, wherein the vestibular malady is selected from the group consisting of vertigo, labyrinthitis, vestibular neuritis, and vestibular hypofunction.

7. The method of claim 1, wherein the vestibular malady is benign paroxysmal positional vertigo.

8. The method of claim 1, wherein the vestibular malady is selected from the group consisting of unilateral vestibular hypofunction and bilateral vestibular hypofunction.

9. The method of claim 1, wherein the vestibular malady is Ménière's disease.

10. The method of claim 1, wherein the second optical region distorts the peripheral vision of the first eye, and wherein the first optical region does not distort the vision of the first eye along the line of sight.

11. The method of claim 1, wherein the first lens imparts tunnel vision to the first eye.

12. The method of claim 1, wherein the first and second optical regions are characterized by first and second distinct optical powers.

13. The method of claim 1, wherein the first optical region is centrally disposed in the field of vision of the first eye, and wherein the second optical region is disposed adjacent to the first optical region.

14. The method of claim 1, wherein the first optical region is centrally disposed in the field of vision of the first eye, and wherein the second optical region is disposed peripheral to the first optical region.

15. The method of claim 1, wherein the first optical region is centrally disposed over the line of sight of the first eye, and wherein the second optical region is disposed over the peripheral vision of the first eye.

16. The method of claim 15, wherein the first and second optical regions produce a condition in the first eye selected from the group consisting of near-sightedness and tunnel vision.

17. The method of claim 1, wherein the eyewear is a pair of eye glasses.

18. The method of claim 1, wherein the eyewear is a pair of contact lenses.

19. The method of claim 1, wherein the eyewear further comprises a second lens which extends over the field of vision of a second eye, and wherein the second lens has third and fourth optical regions therein characterized by third and fourth distinct optical powers.

20. The method of claim 19, wherein the first and third optical powers are the same, and wherein the second and fourth optical powers are the same.

21. The method of claim 1, wherein the first and second optical regions are essentially circular and concentric.

22. The method of claim 21, wherein the second optical region is disposed around the first optical region.

23. The method of claim 1, wherein the first and second regions impart vision to the first eye which is characterized by an undistorted first central vision and a distorted first peripheral vision.

24. The method of claim 1, wherein the first region transmits visible light with a lower degree of optical distortion than said second region.

25. The method of claim 24, wherein the first region transmits visible light with a lower degree of optical distortion than said second region as measured by the ASTM F2156-11 standard test method.

26. The method of claim 1, wherein the first and second regions impart vision to the first eye which is characterized by an uncolored first central vision and a colored first peripheral vision.

27. The method of claim 1, wherein the first and second regions impart vision to the first eye which is characterized by an untinted first central vision and a tinted first peripheral vision.

28. The method of claim 1, wherein the first and second regions impart vision to the first eye which is characterized by a polarized first central vision and an unpolarized first peripheral vision.

29. The method of claim 1, wherein said first region is characterized by a higher % transmission than said second region.

30. The method of claim 1, wherein the first and second regions impart vision to the first eye which is characterized by a first central vision and a first peripheral vision, and wherein the first peripheral vision includes occlusions which specularly or diffusely scatter light over the visible region of the spectrum.

* * * * *